United States Patent [19]

Massie et al.

[11] 3,935,876
[45] Feb. 3, 1976

[54] AIR LEAK DETECTOR

[75] Inventors: Harold Lee Massie, Minnetonka; Louis C. Cosentino, Wayzata, both of Minn.

[73] Assignee: Renal Systems, Inc., Minneapolis, Minn.

[22] Filed: Nov. 15, 1974

[21] Appl. No.: 524,329

[52] U.S. Cl........ 137/177; 128/214 E; 128/DIG. 13; 340/237 R; 356/181; 356/39; 250/573
[51] Int. Cl.².................. A61M 5/14; G08B 21/00
[58] Field of Search.................. 137/154, 177, 183; 128/214 E, DIG. 13; 340/237 R; 356/39, 181; 250/573

[56] References Cited
UNITED STATES PATENTS

| | | | |
|---|---|---|---|
| 2,835,252 | 5/1958 | Mauchel | 128/214 E |
| 3,163,176 | 12/1964 | Darling | 128/214 E X |
| 3,812,482 | 5/1974 | Clark | 128/214 E X |

Primary Examiner—Alan Cohan
Attorney, Agent, or Firm—Merchant, Gould, Smith, Edell, Welter & Schmidt

[57] ABSTRACT

A device for detecting the presence of air bubbles within a fluid-carrying tube, for example a blood tube used in medical procedures. The tube is placed between a light source and an optical sensor which produces signals when bubbles pass through the tube. These signals are integrated and a switch changes state when the integration reaches a predetermined value. The detector thus responds to a predetermined quantity of air, either by a large air bubble or an accumulation of small air bubbles. In a preferred embodiment, the switch releases a springloaded clamp which pinches off the tube when an excessive amount of air is detected.

14 Claims, 4 Drawing Figures

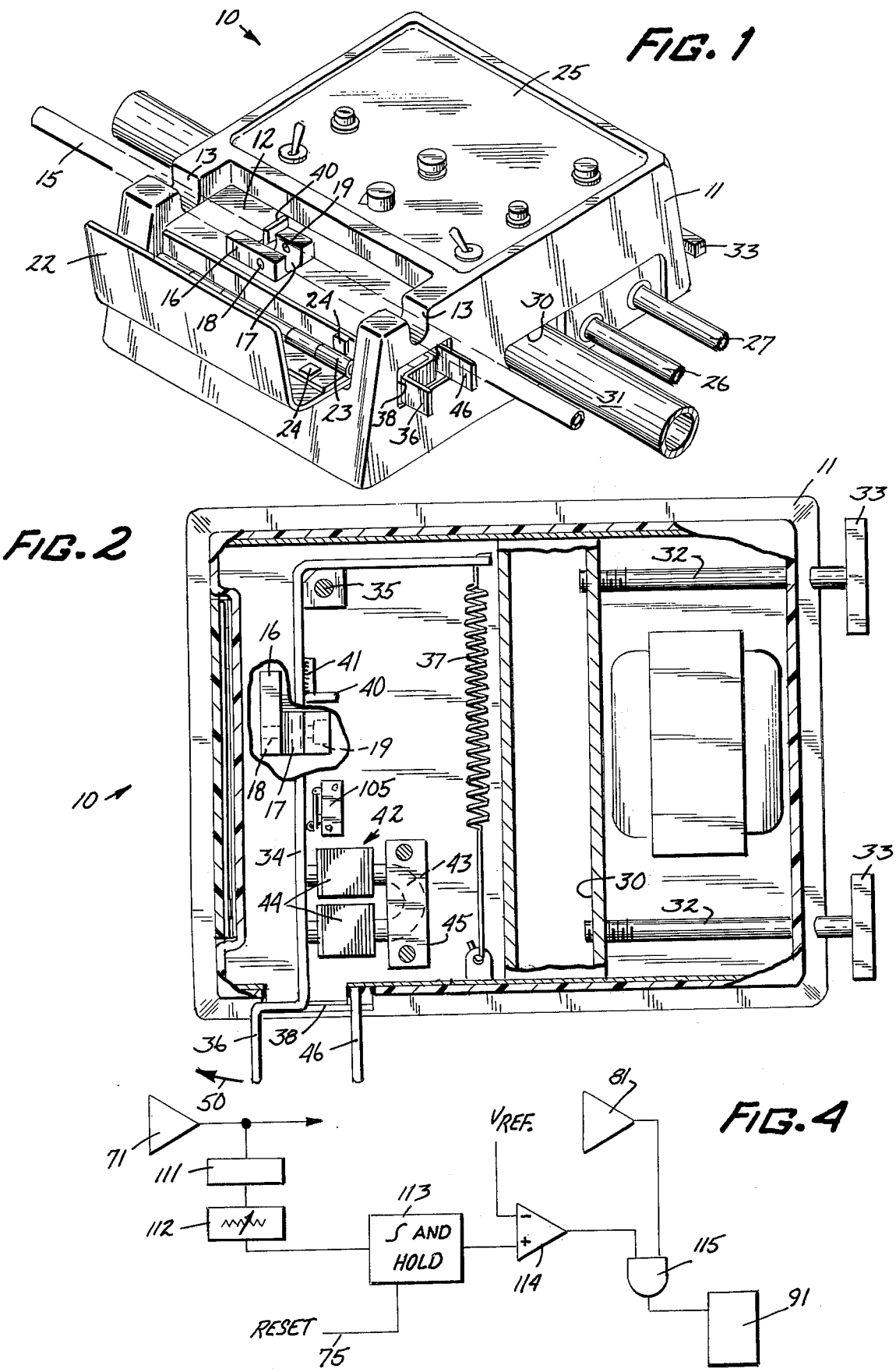

AIR LEAK DETECTOR

BACKGROUND OF THE INVENTION

The present invention pertains generally to the field of air leak detectors for sensing the presence of air bubbles in a fluid. Devices of this general type find an important use in the medical field where they are used for detecting the presence of air bubbles in a tube carrying blood. In many medical and surgical procedures, it is necessary for blood to be transported through tubing outside the patient's body. Examples include the connection of a patient to a heart-lung machine during surgery, or to an artificial kidney machine during hemodialysis.

In the case of hemodialysis, blood from the artery of a patient, usually in his arm, is conveyed through tubing to a dialyzer for purification by dialysis, and then through additional tubing back to the patient's vein. In addition to the dialyzer itself, the blood flow path may include additional elements such as a pump and a flow meter. The development of an air leak anywhere in the external blood flow path could be fatal to the patient, if a large air bubble is allowed to return with the blood to the patient's body. To prevent this a drip chamber is usually connected in the blood flow path to remove any air or other undissolved bubbles in the blood. Additionally, it is desirable to provide some type of air leak detector, preferably at the end of the blood flow path just before it returns to the patient's vein.

One type of prior art safety device intended to prevent return of air to the patient's blood comprises a device to sense the level of blood in the drip chamber. Such devices operate on the theory that so long as the blood level is high enough, no air will be drawn into the return line. However, this type of prior art device can be confused by the presence of foam, and it also suffers from the disadvantage of providing only indirect sensing, as it does not actually sense air bubbles in the return line directly to the patient.

Other types of prior art devices have been designed to sense the presence of an air bubble, and to provide an alarm signal in response thereto. Some of these devices operate by sensing the difference in optical properties between blood and air. Others operate by sensing differences in magnetic or ultrasonic properties of blood and an air bubble. One problem existing with these prior art devices is that they are subject to nuisance alarms. Because either a larger air bubble or a number of small air bubbles can present a dangerous situation to the patient, these prior art devices have been designed with high enough sensitivity to detect small bubbles. However, a few bubbles by themselves, if small enough, can be safely tolerated by the patient, but the prior art sensors will activate their alarms even for a single small bubble. Since these commonly occur from time to time, but represent no real threat to the patient, a number of unnecessary interruptions to the medical procedure result. The prior art systems have not been able to reduce their sensitivity to avoid triggering on small bubbles, since a larger number of small bubbles represents a dangerous condition which must be sensed.

Another problem with prior art air leak sensors is that while they may detect bubbles in blood, in general they are unable to detect air bubbles in the saline solution passed through the tubing during start-up procedures in hemodialysis. Accordingly, these devices provide no protection during the initial phases of a hemodialysis procedure.

The present invention provides an air leak detector which responds not only to the presence of an air bubble, but also to the total volume of the air bubbles detected in a given period of time. Thus, the present invention will trigger its alarm if a large air bubble or column should occur. It will also detect the presence of a small air bubble but instead of triggering its alarm, it will accumulate and keep track of the various volumes of bubbles detected. If the accumulated value exceeds the safe preset value during a given time period, the alarm will be activated.

It is also important that the air leak detecting device itself should be fail-safe in operation, so that a failure on the part of the detector will not put the patient in jeopardy. The present invention accomplishes this goal by providing a spring-loaded clamp for pinching off the blood tube and at the same time physically opening the switch for the blood pump. In normal operation, the clamp is held open by an electromagnet, to be released when an out-of-tolerance quantity of air is detected. However, should the power supply to the detector fail or should some of the circuitry in the detector itself fail, the cutting of power will result in stopping the blood flow to warn of inoperativeness of the detector, rather than allowing the procedure to continue without this important protection.

The present invention senses optical properties of the blood or other fluid in order to detect air bubbles or clots. The detector automatically and continuously adjusts itself for varying optical densities of the fluid being monitored. For example, the hemodialysis process is started with the dialyzer and external blood flow path filled with a saline solution. As the hemodialysis process gets underway, this saline solution is gradually replaced by the patient's blood flowing through the path. The tube carrying fluid to the patient's vein therefore initally contains saline solution, which is clear, then later contains blood which is optically much denser. Automatic circuitry within the present detector changes the operating point of the optical sensing means to accommodate the changing density of the fluid.

In addition, special circuitry enables the detector to respond to bubbles or objects in the fluid which have either greater or lessor light transmitting ability than the fluid. Thus, the detector responds to air bubbles in the saline solution, to air bubbles in blood, or to clots in the blood.

Another feature of the present invention allows it to respond not only to a large bubble or column of air in the tube, representing a gross leak, but also to a series of small micro bubbles. Micro bubbles above a very small minimum threshold size are measured and integrated over a period of time. When a predetermined volume of micro bubbles has been detected, the detector will so indicate. The sensitivity of the detector to different quantities of micro bubbles can easily be selected.

SUMMARY OF THE INVENTION

According to the present invention, there is provided apparatus for detecting the presence of air or other foreign particles in a fluid carrying tube. Optical sensing means placed adjacent the tube produce a signal when an air bubble or other foreign object passes through the tube. An integrator integrates the signals produced by the optical sensing means, and a switching means changes state when the output of the integrator reaches a predetermined value, thereby providing an indication of an out of tolerance condition.

In the preferred embodiment, a spring-loaded clamp adjacent the tube is held open by an electromechanical device. When the switching means changes states, indicating an excessive amount of air in the fluid, the electromechanical device releases the clamp which pinches off the tube thus stopping the flow.

DESCRIPTION OF THE DRAWING

FIG. 1 is a view in perspective of an air leak detector according to the present invention;

FIG. 2 is a top view of the detector of FIG. 1, portions of which are broken away for purposes of clarity;

FIG. 4 is an electrical block diagram of bubble accumulator circuitry which may be used with the circuitry of FIG. 3.

DESCRIPTION OF THE PREFERRED EMBODIMENT

Figure 3:
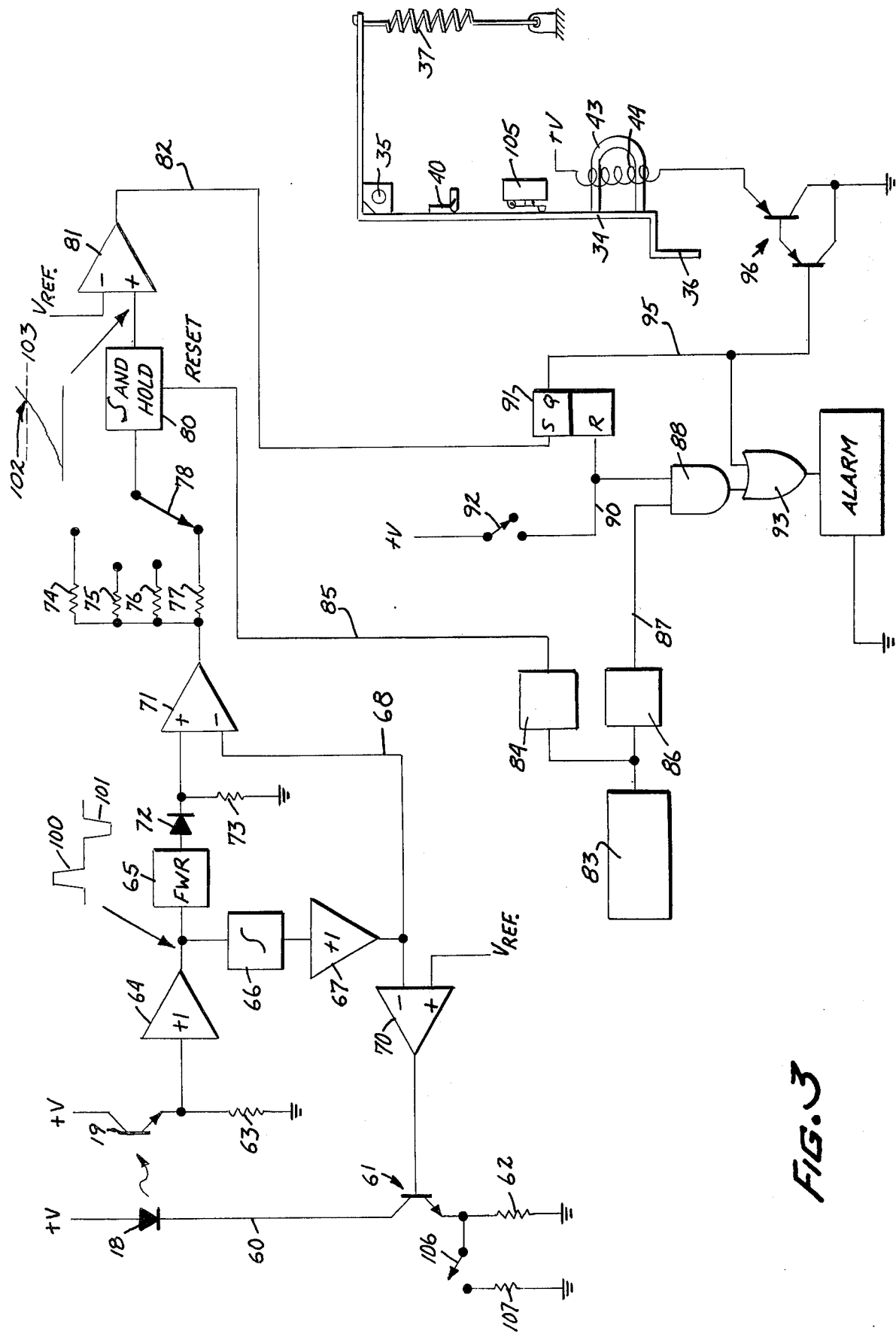
FIG. 3 is an electrical block diagram of the detection circuitry for the detector of FIGS. 1 and 2.

In FIG. 1, detector 10 has a housing 11 which has a well 12 near one end. The walls of the housing on either side of well 12 have a notch or channel 13 for purposes of receiving the blood, or fluid, carrying tube 15. Positioned near the center of well 12 is a sensing block 16, which also contains a channel 17 through which the tube 15 passes. Block 16 contains a light source 18 and a photo detector 17 within bores, positioned on either side of tube 15. A door 22 is attached to the housing by a hinge 23, and is designed to close over well 12 to hold tube 15 in place, and to exclude ambient light from the sensing block area. Magnetic latches 24 are provided for holding the door closed.

On the top of the housing is a control board 25, which contains the various indicator lights and control switches for operating the device. A pair of electrical power lines 26 and 27 connect to the side of the housing. These lines are for supplying electric power to the detector and for suppling electric power to a blood pump, as controlled by the detector.

Referring also now to FIG. 2, most of the top of the detector has been broken away, except for the sensing block 16, to reveal some internal components of the device. The entire detector housing can be clamped to a portion of the bed frame, or to any other suitable support, by means of an inverted U-framed channel 30, along the underside of the housing. In FIG. 1, the detector is shown clamped to a portion of a bed frame 31. In FIG. 2, the supporting screw clamps 32, and handles 33, for attaching the device to bed frame 31 are shown. The area between the clamps 32 may be used for mounting the electrical components as may be necessary, a transformer being shown for example in FIG. 2.

The actuating arm 34 is shown most clearly in FIG. 2. It is a generally L-shaped arm, pivoted at 35, and extending through an opening 38 at the side of the housing, to a tab portion 36. The other end of actuating arm 34 is connected by a spring 37, whose other end is anchored to the housing. Spring 37 is in tension, thereby urging actuating arm 34 in a clockwise direction in FIG. 2.

Tube clamp 40 is seen in both FIGS. 1 and 2. In FIG. 2, the lower portion of the tube clamp is shown welded to the actuating arm 34, at 41. In FIG. 1, the upper portion of tube clamp 40 is shown in alignment with a portion of the sensing block 16, but spaced apart therefrom across channel 17. Spring 37 tends to urge actuating arm 34 so that clamp 40 pinches tube 15 off between clamp 40 and the portion of the sensing block 16. The clamp may be held in an open position by means of an electromagnet 42, which has a U-shaped core 43 and a pair of coils 44. Electromagnet 42 is held in place by a mounting bracket 45 so that the ends of core 43 will contact the actuating arm 34 when it is pulled back in a counter-clockwise direction against the spring 37. A stationary tab 46 is provided on the housing, projecting through the opening 38, so that the actuating arm can be set by pulling together the actuating arm tab 36 and the stationary tab 46 with the thumb and fingers. Once the actuating arm is pulled against the electromagnet, and the electromagnet is energized, it has sufficient magnetic power to hold the actuating arm so the clamp is open.

In both FIGS. 1 and 2, the actuating arm is shown with the clamp in the open position. If an air bubble is detected, the power to the electromagnet 42 is shut off allowing spring 37 to move the actuating arm 34 in the direction indicated by arrow 50, thereby bringing clamp 40 against the sensing block 16 to pinch off the blood tube 15. The spring and actuating arm are preferably designed so as to provide a force of about 14 pounds at the clamp, to insure that no fluid continues to flow after the clamp has been released.

Referring now to FIG. 3, the operating circuit of the preferred embodiment will now be explained. In the preferred embodiment, the optical sensing means comprises a phototransistor 19 which receives light from a light-emitting diode 18 as transmitted through the blood carrying tube (15 in FIG. 1). Current for operating the various circuits shown in FIG. 3 is provided by a suitable power supply, not shown, but indicated as +v. The power supply voltage is connected to the anode of light-emitting diode 18 and the cathode is connected by a lead 60 to the collector of a transistor 61, which serves as a current source. The emitter of this transistor connects through a resistor 62 to signal ground to complete the circuit. The amount of current drive supplied to diode 18 is controlled by transistor 61, as will be explained hereinafter.

The collector of phototransistor 19 connects to the power supply and its emitter connects through a resistor 63 to ground. The emitter of transistor 19 also connects to the input of an amplifier 64. In the preferred embodiment, this amplifier has a voltage gain of one and serves principally to provide load isolation between phototransistor 19 and the circuits which follow. The output of amplifier 64 connects to a full wave rectifier 65 and also to the input of an integrator 66. The output of integrator 66 connects to the input of an amplifier 67, which in the preferred embodiment has a voltage gain of one and serves mainly to match impedances and provide load isolation. The output of amplifier 67 connects to a lead 68, which connects to the inverting or minus input of differential amplifiers 70 and 71. The non-inverting input of amplifier 70 is connected to a reference voltage and its output connects to the base of transistor 61. The reference voltage connected to amplifier 70, and the gain or amplifier 70, are selected to provide transistor 61 with the desired drive current to operate diode 18 with sufficient light output so that transistor 19 will be biased to operate somewhere near the midpoint of its conductive range.

Thus, the loop which includes integrator 66, amplifier 70 and transistor 61 serves as an automatic gain control to automatically adjust the operating point of phototransistor 19. Integrator 66 tends to make the circuit respond to the average signal output of phototransistor 19 and does not respond fast enough to change the diode drive in response to individual micro bubbles being sensed. Rather, the gain circuit including integrator 66 responds to the average level of illumination being received by phototransistor 19. Thus, when saline solution is being circulated through tube 15, a great deal of the light transmitted by diode 18 is received by phototransistor 19. This generally high level of illumination tends to create a larger signal in the feedback loop through amplifier 67. The inverting property of amplifier 70 is used to provide a decreasing drive to transistor 61, which then reduces the current to, and amount of light produced by, diode 18. On the other hand, when blood beings to replace the saline solution in tube 15, the general amount of illumination reaching phototransistor 19 will be decreased, because of the greater optical density of blood. This tends to create a decreasing signal through the loop up to the output of amplifier 67. Again the inverting property of amplifier 70 therefore increases the drive to transistor 61, to increase the amount of illumination being provided by transistor 18. This is necessary in order to prevent a state of operation in which phototransistor 19 might be either totally into saturation on the one hand, or into cutoff on the other, either of which would render it insensitive to changes in the illumination level caused by passage of bubbles.

The output signal from amplifier 64 is rectified by full wave rectifier 65, for reasons which will be explained hereinafter. The output of rectifier 65 passes through a diode 72, a load resistor 73 to ground, and to the non-inverting input of differential amplifier 71. The output of this amplifier connects to a plurality of sensitivity scaling resistors 74, 75, 76 and 77, which connect to terminals of a selector switch. The pole 78 of the switch connects to the input of an integrate and hold circuit 80.

The output of circuit 80 connects to the non-inverting of a comparator, or differential amplifier, 81. The inverting input of comparator 81 is connected to a reference voltage and its output connects to a lead 82.

A timer 83 is provided which, in the preferred embodiment, provides a timing pulse every sixty seconds. This timing circuit may be, for example, a unijunction timing circuit, or any other known type of timer. The output pulses from timer 83 are shaped and stretched as necessary by a wave-shaping circuit 84, then applied via lead 85 to a reset input of integrate and hold circuit 80. The timing pulses are also applied to a second waveshaping and pulse stretching circuit 86, which stretches the pulses to a duration of two seconds each. These lengthened pulses are then applied by lead 87 to one input of an AND gate 88. The other input of AND gate 88 is connected to a lead 90 which also connects to the reset input of a flip-flop circuit 91. Lead 90 also connects to one terminal of a control switch 92 whose pole is connected to a voltage source +v. The output of AND gate 88 connects to one input of an OR gate 93, whose output connects to an alarm buzzer 94.

Lead 82 from comparator 81 connects to the set input of flip-flop 91. The Q output from flip-flop 91 connects to a lead 95, which in turn connects to the other input of OR gate 93, and to the base of a PNP power darlington transistor pair 96. The collector of the transistor pair connects to ground, and the emitter connects through coil 44 of electromagnet 42 to +v.

The operation of the circuitry at detecting bubbles will now be explained. As previously indicated, the signal at the output of amplifier 64 represents the immediate illumination level received by transistor 19 while the signal at lead 68 represents the average illumination as integrated over a period of time by integrator 66. If an air bubble passes between the light source and transistor 19 during a blood flow, the greater light transmitting ability of the air will result in a positive going pulse, as indicated by wave form 100. This pulse is not immediately reflected at lead 68 because of the time integrating property of integrator 66. On the other hand, if a blood clot should pass through the tube, its greater optical density would result in a lessening of light intensity being received by transistor 19 and would result in a negative going pulse, indicated at 101. Similarly, if the tube were filled with saline solution, and an air bubble passed therethrough, the lesser light transmission of the air bubble would result in a negative going pulse, as indicated by wave form 101.

Full wave rectifier 65 is provided so that the circuit will respond in either case to clots or bubbles in blood, or to bubbles in saline. Negative pulses are rectified to positive pulses, then all pulses are passed through diode 72 which serves as a threshold setting device. Diode 72 has a forward bias voltage drop of approximately 0.6 of a volt. Additional diodes or other types of voltage offset devices could be used to provide the threshold adjustment.

In normal operation, in the absence of an air bubble, the voltage at the immediate output of rectifier 65 and the voltage on lead 68 will be equal, since the instantaneous signal and the average signal will be the same. These two signals are fed into the differential amplifier 71 for comparison, except that the instantaneous signal is dropped across the 0.6 volt threshold provided by diode 72. The result is that, in the absence of an air bubble, the voltage applied to the non-inverting input is slightly less than the voltage applied to the inverting input, resulting in a low output from amplifier 71. When an air bubble or clot is detected, resulting in a positive or negative pulse 100 or 101, the input to the non-inverting input of amplifier 71 will go positive, causing the output of differential amplifier 71 to go to a high value. It is apparent that the smallest bubble or other object to be detected is fixed by the offset voltage provided by diode 72, which effectively sets the threshold of the device. By way of example, in the preferred embodiment, the 0.6 voltage threshold corresponds to a minimum bubble size of 0.05 cubic centimeters of air, and this represents the lower response threshold of the system. If necessary, the response can be adjusted by changing the voltage offset.

Switch 78 selects one of the scaling resistors to determine the triggering sensitivity of the circuit. Preferably, this switch is operator adjustable from the front panel, and the resistance values are chosen to correspond to tolerance levels which will be acceptable in various common modes of operation. The output of amplifier 71, as scaled by one of resistors 74–77, is applied to the integrate and hold circuit 80. This circuit integrates upwards when a signal is applied, at a rate determined by which of resistors 74–77 is selected, and to an extent corresponding to the duration of the pulse, i.e. the size of the bubble. In the absence of a signal, the value attained is held until eventually the circuit is reset by pulse from lead 85, at which time the integration cycle begins again.

Thus, if no bubbles at all are detected, no value is built up in integrator 80, and its output remains low. However, if a series of very small micro bubbles are detected, the integrator will integrate upward a small amount of each bubble depending upon the size of the bubble and its duration in front of the phototransistor. A series of small micro bubbles is indicated by the lower portion of wave form 102 giving a stair-step effect. The upper portion of wave form 102 indicates the response to a large bubble or column of air, in which case the integrator integrates very rapidly up to a triggering value indicated by dotted line 103. This triggering value is set by the reference voltage applied to the inverting input of differential amplifier, or comparator, 81. This reference voltage is selected in terms of the permissible amount of micro bubble buildup in a one minute time period between successive resettings of the integrate and hold circuit. Of course, if a large bubble or column of air is encountered, the integrator will be driven up to the trigger level very quickly to trigger the comparator. On the other hand, the number of micro bubbles detected in a one minute period which will result in triggering the alarm is determined by the value of reference voltage applied to amplifier 81, as well as the scaling resistors switched into the circuit. For example, the reference voltage and the scaling resistors may be selected in the preferred embodiment to give an adjustable triggering level corresponding to 0.1cc to 3cc total volume of air detected in a 1 minute interval.

In the preferred embodiment, comparator 81 is an open loop operational amplifier so it effectively acts as a switching means to change states rapidly when the integrated signal from circuit 80 exceeds the reference voltage. When this happens, the voltage on lead 82 suddenly goes positive, thereby setting flip-flop 91. This causes the output of the flip-flop to go positive which activates alarm 94, and also turns off darlington transistor pair 96, allowing actuating arm 34 to fly away from the electromagnet and pinch off the tube.

At the same time the movement of actuating arm 34 opens a momentary contact switch 105, which is in contact with arm 34, as shown in FIGS. 2 and 3. This switch is used to control the operation of the blood pump located elsewhere in the blood flow path so that the pump will be stopped immediately when the clamp is applied.

The overall operation of the detector device will now be explained. The device is secured to a suitable support such as a bedpost very near the patient, so that it can monitor the very tail end of the external blood path just before the blood reenters the patient's vein. A tube containing the return blood flow to the vein is positioned within the tube-receiving channel 13 (FIG. 1) and 17, and the door 22 is closed to hold the tube in place, and to exclude extraneous light from the photosensor. The power to the detector is turned on and the blood pump which is used in the external path is connected via the power line 27 which connects to the switch 105 so that the pump will be under control of the air leak detector. The operation is initiated by turning a front panel switch to bypass mode. With reference to FIG. 3, this switches, switch 92 to apply +v to lead 90, resetting flip-flop 91 and enabling AND gate 88. With AND gate 88 enabled, periodic pulses from timer 83 will be applied through OR gate 93 to the alarm buzzer 94. Thus, when the circuit is in bypass mode, a 2-second buzz will be sounded every minute, to indicate to the operating personnel that the air leak detector is not in operation but is being bypassed.

The resetting of flip-flop 91 puts ground or low signal on lead 95, turning on darlington pair 96 to energize electromagnet 42.

The operator then pulls the actuating arm tab 36 towards the stationary tab 46 and the electromagnet latches and holds the actuating arm 34. At the same time, switch 105 is closed allowing the pump motor to start.

To test the operation of the detector circuit, a switch 106 is provided (FIG. 3). When moved to the test position, switch 106 switches a smaller resistor 107 in parallel with resistor 62, in connection to the emitter of transistor 61. Pushing switch 106 thus results in a sudden increase in current to LED 18, and a pulse of light to phototransistor 19. If the circuit is operating properly, the pulse propagates through the circuitry running up integrator 80 and triggering comparator 81. This causes flip-flop 91 to set, thus sounding alarm 94 and dropping out electromagnet 42. This results in the motor being stopped and the tube being pinched off. With the test being completed, switch 106 is released, switch 92 is moved to the armed mode (as shown in FIG. 3), actuating arm tab is pulled back to the electromagnet again opening the clamp, and operation proceeds. If an air bubble in the saline solution, or an air bubble or clot in the blood is detected, the tube will be clamped off, the pump will be stopped, and the alarm will sound, as previously explained.

It may be desirable to provide another circuitry in addition to the sample and hold circuit 80 which responds to a count of the number of bubbles detected. This can be accomplished by counting or accumulating the number of pulses appearing at the output of comparator 71 in FIG. 3. Digital or analog techniques can be employed as desired for this purpose.

In FIG. 4, there is shown an analog accumulating circuit which responds to the number of bubbles counted by the detector during a given time interval. The circuitry of FIG. 4 is intended to be added to the circuitry previously described in FIG. 3. In FIG. 4, differential amplifier 71, comparator 81, and flip-flop 91 are the same components previously described with reference to FIG. 3. The additional circuitry comprises a standard pulse width circuit 111, a sensitivity adjusting means 112, another integrate and hold circuit 113, which is substantially identical to circuit 80 of FIG. 3, and another comparator 114 which is similar in operation to comparator 81 of FIG. 3. Output pulses from amplifier 71 may be fed not only to integrate and hold circuit 80 of FIG. 3, but also to the standard pulse width circuit 111 of FIG. 4. This circuit may be a one shot, or a simple differentiator, and its purpose is to produce a pulse of constant duration upon receipt of a pulse of variable duration from the output of amplifier 71. Circuit 111 thus removes the weighting effect of the duration of the pulses, so that the circuitry of FIG. 4 responds only to the number of the pulses.

Standardized pulses from circuit 111 pass through circuit 112 to integrate and hold circuit 113, which operates as previously described with respect to circuit 80. Sensitivity adjustment 112 may be an adjustable resistor, or it may be a selector switch similar to switch 78 of FIG. 3 and associated resistors. Comparator 114 connects to the output of circuit 113, and compares the developed voltage against a reference voltage. Upon occurrence of each bubble, without regard to the size of the bubble, a given increment will be integrated upward and held in circuit 113. When a predetermined amount, determined by the reference voltage applies to comparator 114 is reached, the comparator will change states. The integrate and hold circuit 113 may be periodically reset by a pulse from lead 75, as in FIG. 3.

If the circuitry of FIG. 4 is to be used, it can be added into the circuitry of FIG. 3 by providing an additional AND gate 115 connected in lead 82 ahead of flip-flop 91. AND gate 115 would then receive as its input, the outputs of comparators 81 and 114. Thus, the alarm would be triggered either by build-up of an excessive volume of air or by an excessive number of small bubbles. Such a feature may be useful in some cases for detecting a large number of micro bubbles. While the embodiment shown in FIG. 4 is in analog form, the same function could easily be achieved by appropriate digital circuitry to count the pulses at the output of amplifier 71.

One of the safety features of the present invention will be apparent in that should the power supply to the detector fail, the tube will be clamped off and the pump will stop. Electrical power is used to hold the clamp open, but the more reliable spring power is used to pinch it off. Thus, in the event of the loss of electrical power to the detector it will deenergize in a safe condition.

In summary, the present invention provides a highly efficient and reliable air leak detector suitable for use in monitoring blood lines. The detector according to the present invention will not only respond to gross bubbles or air columns, but will also respond to a selectable build-up of micro bubbles over a given time interval. Further, the detector responds not only to bubbles in blood, but to bubbles in saline solution passed through the tube, and also to blood clots or other foreign bodies which may appear in the blood.

What is claimed is:

1. Apparatus for detecting presence of air in a fluid carrying tube, comprising:
   a. optical sensing means for producing a signal in response to an air bubble in the fluid carrying tube;
   b. integrating means connected to receive signals from said optical sensing means and operable to integrate said signals; and
   c. switching means connected to said integrating means, said switching means operable to change states when the integrated signal reaches a predetermined value, thereby providing an indication of excessive air in the fluid.

2. Apparatus according to claim 1 further including clamp means connected to said switching means, said clamp means operable to clamp off flow in the tube when said switching means changes states, thereby preventing flow of fluid when excessive air is present.

3. Apparatus according to claim 1 further including reset means connected to said integrating means for periodically resetting said integrating means, whereby said air detecting apparatus responds to the total volume of air detected during a measurement period.

4. An air leak detector comprising:
   a. a housing;
   b. means in said housing defining a tube receiving channel for receiving a blood carrying tube;
   c. tube clamp means positioned adjacent said channel;
   d. an actuating arm movably mounted adjacent said channel opposite said tube clamp;
   e. spring biasing means attached to said actuating arm for urging said arm toward said clamp across said channel;
   f. electrically operated means for selectively holding said actuating arm away from said tube clamp;
   g. optical sensing means mounted adjacent the channel for producing a signal in response to an air bubble in the blood carrying tube;
   h. integrating means connected to receive signals from said optical sensing means and operable to integrate said signals; and
   i. switching means connected to said integrating means and to said electrically operated means, for releasing said actuating arm to clamp the tube when the integrated signal reaches a predetermined value, indicating an excessive amount of air in the blood.

5. Apparatus according to claim 4 further including a pump switch positioned on said housing adjacent said actuating arm for activation thereby, said pump switch being closed when said actuating arm is in its open position, and being opened when said actuating arm is closed against said tube clamp.

6. Apparatus according to claim 4 further including a door pivotally mounted to said housing for closing over the tube receiving channel to hold the tube in place and shield the optical sensing means from stray light.

7. Apparatus according to claim 4 further including alarm means connected to said switching means and operable to produce an alarm signal when the switching means changes states.

8. Apparatus according to claim 1 wherein said optical sensing means comprises a light emitting diode positioned on one side of the tube receiving channel and a photo transistor positioned on the other side of the tube receiving channel in alignment with said light emitting diode.

9. Apparatus according to claim 8 wherein said optical sensing means further includes an automatic biasing circuit for supplying drive current to the light emitting diode according to the average illumination by the photo transistor.

10. Apparatus according to claim 8 wherein said integrating means includes a signal scaling means for varying the sensitivity of the integrator, whereby the sensitivity of the air leak detector can be adjusted over a range of values.

11. Apparatus according to claim 10 further including reset means connected to said integrating means for periodically resetting the integrating means.

12. Apparatus for detecting presence of air in a fluid carrying tube, comprising:
   a. sensing means for producing a signal in response to an air bubble in the fluid carrying tube;
   b. integrating means connected to receive signals from said sensing means and operable to integrate said signals;
   c. switching means connected to said integrating means, said switching means operable to change states when the integrated signal reaches a predetermined value, thereby providing an indication of excessive air in the fluid; and
   d. clamp means connected to said switching means, said clamp means operable to clamp off flow in the tube when said switching means changes states, thereby preventing flow of fluid when excessive air is present.

13. An air leak detector comprising:
   a. a housing;
   b. means in said housing defining a tube receiving channel for receiving a blood carrying tube;
   c. tube clamp means positioned adjacent said channel;
   d. an actuating arm movably mounted adjacent said channel opposite said tube clamp;
   e. spring biasing means attached to said actuating arm for urging said arm toward said clamp across said channel;
   f. electrically operated means for selectively holding said actuating arm away from said tube clamp;
   g. sensing means mounted adjacent the channel for producing a signal in response to an air bubble in the blood carrying tube;
   h. integrating means connected to receive signals from said sensing means and operable to integrate said signals; and
   i. switching means connected to said integrating means and to said electrically operated means, for releasing said actuating arm to clamp the tube when the integrated signal reaches a predetermined value, indicating an excessive amount of air in the blood.

14. Apparatus according to claim 13 further including a pump switch positioned on said housing adjacent said actuating arm for activation thereby, said pump switch being closed when said actuating arm is in its open position, and being opened when said actuating arm is closed against said tube clamp.

* * * * *